(12) United States Patent
Homer

(10) Patent No.: US 11,559,353 B1
(45) Date of Patent: Jan. 24, 2023

(54) ABLATIVE SKIN RESURFACING WITH TOPICAL RADIATION BLOCK

(71) Applicant: Gregg S. Homer, Laguna Beach, CA (US)

(72) Inventor: Gregg S. Homer, Laguna Beach, CA (US)

( * ) Notice: Subject to any disclaimer, the term of this patent is extended or adjusted under 35 U.S.C. 154(b) by 2075 days.

(21) Appl. No.: 14/676,705

(22) Filed: Apr. 1, 2015

Related U.S. Application Data

(60) Provisional application No. 61/973,783, filed on Apr. 1, 2014.

(51) Int. Cl.
*A61B 18/20* (2006.01)
*A61B 18/00* (2006.01)

(52) U.S. Cl.
CPC ...... *A61B 18/20* (2013.01); *A61B 2018/0047* (2013.01); *A61B 2018/00577* (2013.01)

(58) Field of Classification Search
CPC .. A61B 2018/00577; A61B 2018/0047; A61B 18/20; A61B 18/203
See application file for complete search history.

(56) References Cited

U.S. PATENT DOCUMENTS

| | | | | |
|---|---|---|---|---|
| 6,050,990 A | * | 4/2000 | Tankovich | A61B 18/203 606/16 |
| 6,086,580 A | * | 7/2000 | Mordon | A61N 5/062 606/9 |
| 6,447,503 B1 | * | 9/2002 | Wynne | A61B 18/20 606/9 |
| 7,201,765 B2 | | 4/2007 | McDaniel | |
| 7,232,456 B2 | | 6/2007 | Chernoff | |

(Continued)

*Primary Examiner* — Mallika D Fairchild
*Assistant Examiner* — Shreya Anjaria

(57) ABSTRACT

The present invention uses one or more radiation-emitting devices in combination with a topical radiation block to ablate the skin and remove topographic variations in the skin surface. The energy pathway may be guided by a computer. The device might also include a treatment plate or window to be placed against the skin in order to flatten the skin surface during treatment. The purpose of the topical radiation block is to manage the areas to which the radiation is applied to the skin by allowing the radiation to reach some portions of the skin, while limiting or preventing the radiation from reaching other portions of the skin. In the case of atrophic scarring, for example, the block may be deposited selectively into the atrophic indentations, such that the block limits or prevents the radiation from reaching (and thereby ablating) the indentations, but allows the radiation to reach (and thereby ablate) the surrounding skin tissue. By ablating only the surrounding tissue, the z of the surrounding tissue is reduced, eventually minimizing or eliminating differences in the skin's topography between the indentations and the surrounding tissue. In the case of hypertrophic scarring, the block may be applied selectively to the surrounding tissue, such that the block limits or prevents the radiation from reaching (and thereby ablating) the scars, but allows the radiation to reach (and thereby ablate) the scars. By ablating only the scars, the z of the scars is reduced, eventually minimizing or eliminating differences in the skin's topography between the scars and the surrounding tissue.

5 Claims, 18 Drawing Sheets

(56) References Cited

U.S. PATENT DOCUMENTS

| | | |
|---|---|---|
| 8,535,299 B2 | 9/2013 | Giovannoli |
| 9,780,518 B2 * | 10/2017 | Sierra ................. H01S 3/08054 |
| 2005/0203593 A1 * | 9/2005 | Shanks ................ A61N 5/0616 |
| | | 606/9 |
| 2008/0058783 A1 * | 3/2008 | Altshuler ............... A61B 18/20 |
| | | 606/9 |
| 2008/0132886 A1 * | 6/2008 | Cohen .................. A61B 18/203 |
| | | 606/34 |
| 2011/0184322 A1 * | 7/2011 | Brawer .................... A61N 7/02 |
| | | 601/3 |
| 2014/0005644 A1 * | 1/2014 | Karni .................. A61B 18/203 |
| | | 606/9 |
| 2014/0081356 A1 * | 3/2014 | Fedorov ................. A61N 5/062 |
| | | 607/88 |

\* cited by examiner

* May be device, handset, galvo mirror(s), or other pathway delivery device.

* May be device, handset, galvo mirror(s), or other pathway delivery device.

* May be device, handset, galvo mirror(s), or other pathway delivery device.

\* May be a radiation-emitting device, handset, galvo mirror(s), or other pathway delivery device.

US 11,559,353 B1

ABLATIVE SKIN RESURFACING WITH TOPICAL RADIATION BLOCK

CROSS-REFERENCE TO RELATED APPLICATIONS

This patent application claims the benefit of U.S. Provisional Application No. 61/973,783, filed Apr. 1, 2014, which is incorporated by reference along with all other references cited in this application.

BACKGROUND OF THE INVENTION

Unsightly scarring of the skin can be a source of emotional distress for many people. Such scarring can take several forms, including hypertrophic (raised) scarring (including keloid scarring), atrophic (sunken) scarring, and striae scarring (including stretch marks). Examples of atrophic scarring include acne, chickenpox, *staphylococcus* (or MRSA), surgical, and injury scarring.

Interest in using lasers to improve the appearance of scars dates back to the early 1980s, when Rox Anderson and John Parrish introduced selective photothermolysis, a process whereby laser energy achieves localized photothermal injury of a targeted chromophore. Early implementations of this technology used ablative, continuous-wave argon, CO(2), and Nd:YAG, as well as the 585-nm pulsed-dye laser (PDL) and a combination of CO(2) and PDL treatment.

There is no general agreement on the mechanism of action by which lasers improve the appearance of scars. Possible mechanisms include (a) laser-induced microvasculature damage leading to tissue hypoxia with subsequent collagen degradation via release of collagenase, (b) thermal damage to collagen fibers dissipated from adjacent vessels with dissociation of disulfide bonds and collagen realignment, and (c) increased regional mast cells, which may serve to stimulate collagen remodeling.

In most cases, improvement to the appearance of scars results from a combination of ablation and collagen regeneration to smooth the skin topography. In the case of complex scar patterns, this can require the use of multiple lasers with small spots and precise exposure for precise durations based on scar thickness, location, and color and patient skin type. In the case of atrophic scars, the goals are (a) to soften the transition between the atrophic indentation and the surrounding skin by ablating the surrounding skin to the depth of the indented region, and (b) to stimulate collagen production within the indented region, requiring precise application of two different laser devices and mechanisms of action. These methods can be time consuming, difficult to perform, and imprecise and can deliver inconsistent results.

Based on the foregoing, a need exists for a method and device that can be performed more quickly, more easily, and with greater precision and more consistent results.

BRIEF SUMMARY OF THE INVENTION

The present invention uses one or more radiation-emitting devices in combination with a topical radiation block to ablate the skin and remove topographic variations in the skin surface. The energy pathway may be guided by a computer. This can be accomplished by any number of methods, including moving the entire radiation-emitting device, utilizing a movable radiation pathway source such as a fiber-optic cable and hand piece, or directing the radiation pathway to one or more mirrors and manipulating the position of those mirrors (such as galvos mirrors). The device might also include a plate or treatment plate or window to be placed against the skin in order to flatten the skin surface during treatment. This plate or window may, without limitation, be part of a handset or part of the device itself.

The purpose of the topical radiation block is to manage the areas to which the radiation is applied to the skin by allowing the radiation to reach some portions of the skin, while limiting or preventing the radiation from reaching other portions of the skin. In the case of atrophic scarring, for example, the block may be deposited selectively into the atrophic indentations, such that the block limits or prevents the radiation from reaching (and thereby ablating) the indentations, but allows the radiation to reach (and thereby ablate) the surrounding skin tissue. By ablating only the surrounding tissue, the z of the surrounding tissue is reduced, eventually minimizing or eliminating differences in the skin's topography between the indentations and the surrounding tissue.

In the case of hypertrophic scarring, the block may be applied selectively to the surrounding tissue, such that the block limits or prevents the radiation from reaching (and thereby ablating) the scars, but allows the radiation to reach (and thereby ablate) the scars. By ablating only the scars, the z of the scars is reduced, eventually minimizing or eliminating differences in the skin's topography between the scars and the surrounding tissue.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
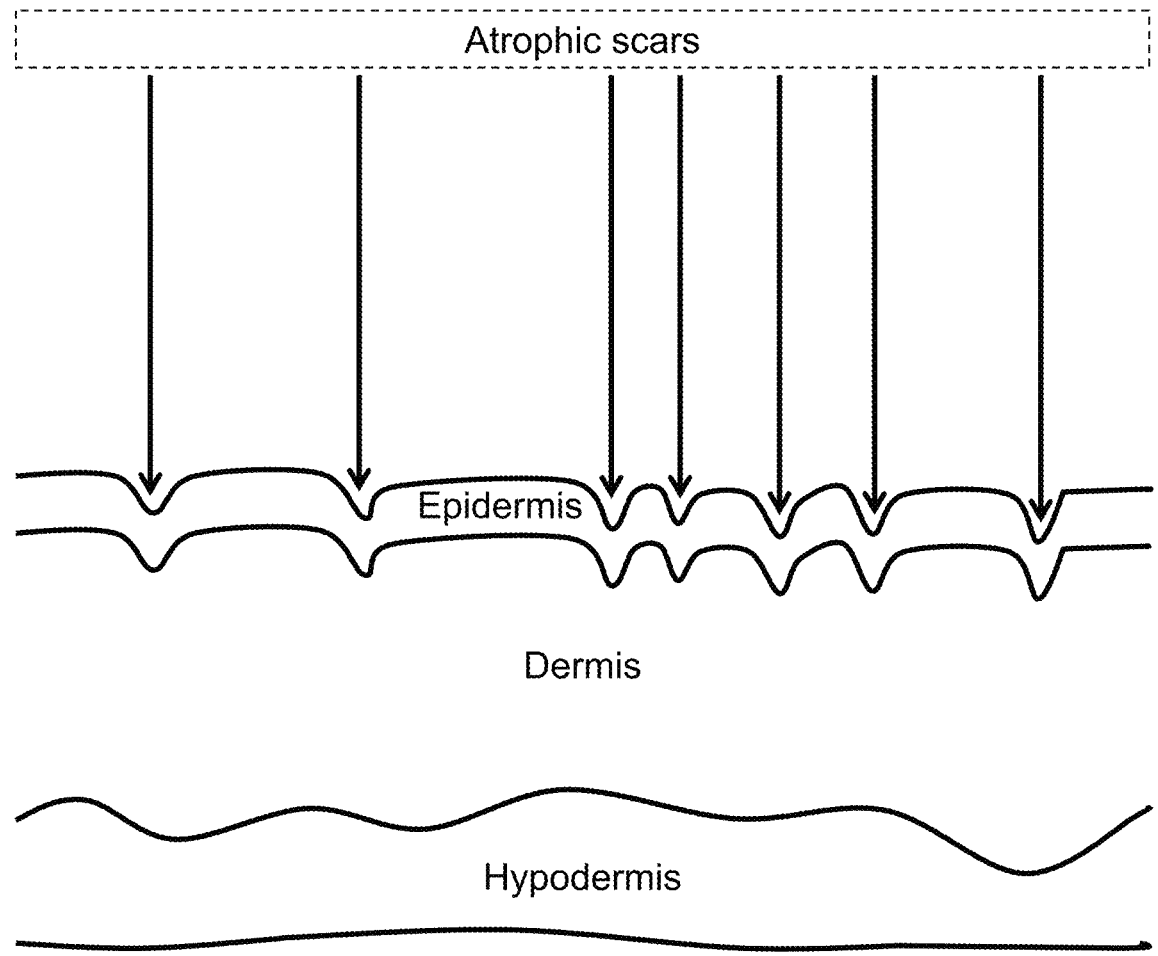
FIG. 1 shows atrophic scars.

The present invention uses one or more radiation-emitting devices (as defined below) in combination with a topical radiation block to ablate the skin and remove topographic variations in the skin surface. "Radiation-emitting device" herein means any device which, when in operation, contains or acts as part of an electronic circuit and emits radiation (as defined below) or, in the absence of effective shielding or other controls, would emit radiation. "Radiation" herein means (a) any ionizing or non-ionizing electromagnetic or particulate radiation or (b) any sonic, infrasonic, or ultrasonic wave radiation-emitting device.

Ablation may be effected in all or any portion of the epidermis, dermis, hypodermis tissue, or any combination of the foregoing. Dermal ablation may be effected in all or any portion of the reticular dermis, the papillary dermis, or both.

The present invention includes any and all radiation-emitting devices capable of ablating skin tissue, including epidermis, reticular dermis, papillary dermis, or hypodermis tissue. Suitable skin-ablative radiation-emitting devices might include, without limitation, lasers with the following gain media: Er:YAG; CO; CO(2); diode; Nd:YAG; Nd:YLF; Nd: YVO(4); Nd:YCOB; Nd:Glass; dye (including, without limitation, stilbene; coumarin; and rhodamine 6G); argon; xenon ion; excimer (including, without limitation, Ar(2), Kr(2), Xe(2), XeBr, KrCl ArF; KrF; XeCl; and XeF); copper vapor; gold vapor; ruby; Ce:LiSAF; Ce:LiCAF; free-electron; gas-dynamic; and nickel-like samarium.

The present invention includes radiation-emitting devices of all wavelengths, including, without limitation, wavelengths within the following ranges, each of which is inclusive of its endpoints: 0-50 nm; 50-100 nm; 100-150 nm; 150-200 nm; 200-250 nm; 250-300 nm; 300-350; nm; 350-400 nm; 400-450 nm; 450-500 nm; 500-600 nm; 600-700 nm; 700-800 nm; 800-900 nm; 900-1,000 nm; 1,000-1,200 nm; 1,200-1,500 nm; 1,500-2,000 nm; 2,000-5,000 nm; 5,000-10,000 nm; 9,000-11,000 nm; and 10,000-20,000 nm.

The present invention also includes radiation-emitting devices of all orders of harmonic generation, including, without limitation, the following: low order; high order; first order; second order; third order; fourth order; fifth order; sixth order; seventh order; eighth order; ninth order; tenth order; eleventh order; and twelfth order.

The present invention includes both continuous wave and pulsed radiation-emitting devices. Pulsed-width radiation-emitting devices include, without limitation, pulse widths within the following ranges, each of which is inclusive of its endpoints: 1-999 as; 1-999 fs; 1-999 ps; 1-999 ns; 1-999 us; and 1-999 ms.

The present invention also includes (a) spot sizes of any and all shapes, including, without limitation, square, ellipsis, circular, triangle, rectangle, diamond, and trapezoid, and (b) spot sizes within the following diameter ranges, each of which is inclusive of its endpoints: 0-5 um; 5-10 um; 10-20 um; 20-30 um; 30-40 um; 40-50 um; 50-100 um; 100-200 um; 200-300 um; 300-500 um; 500 um-1 mm; 0-5 mm; 5-10 mm; 10-20 mm; 20-30 mm; 30-40 mm; 40-50 mm; 50-100 mm; 100-200 mm; 200-300 mm; 300-500 mm; 500 mm-1 cm; and 1 cm-10 cm. Spots generated by the present invention may be separated, tangent, and/or overlapping, and the foregoing spatial relationships may be horizontal, vertical, diagonal, or in any other direction. Spots may overlap within the following ranges, each of which is inclusive of its endpoints: 0-10%; 10-20%; 20-30%; 30-40%; 40-50%; 50-75%; and 75-100%.

The present invention includes energy pathway profiles of any shape, including, without limitation, collimated, Gaussian, and super-Gaussian, flattened-Gaussian, Fermi-Dirac, and super-Lorentzian.

The energy pathway may be guided by a computer. This can be accomplished by any number of methods, including moving the entire radiation-emitting device, utilizing a movable radiation pathway source such as a fiber-optic cable and hand piece, or directing the radiation pathway to one or more mirrors and manipulating the position of those mirrors (such as galvos mirrors) (see FIG. 16).

Figure 7:
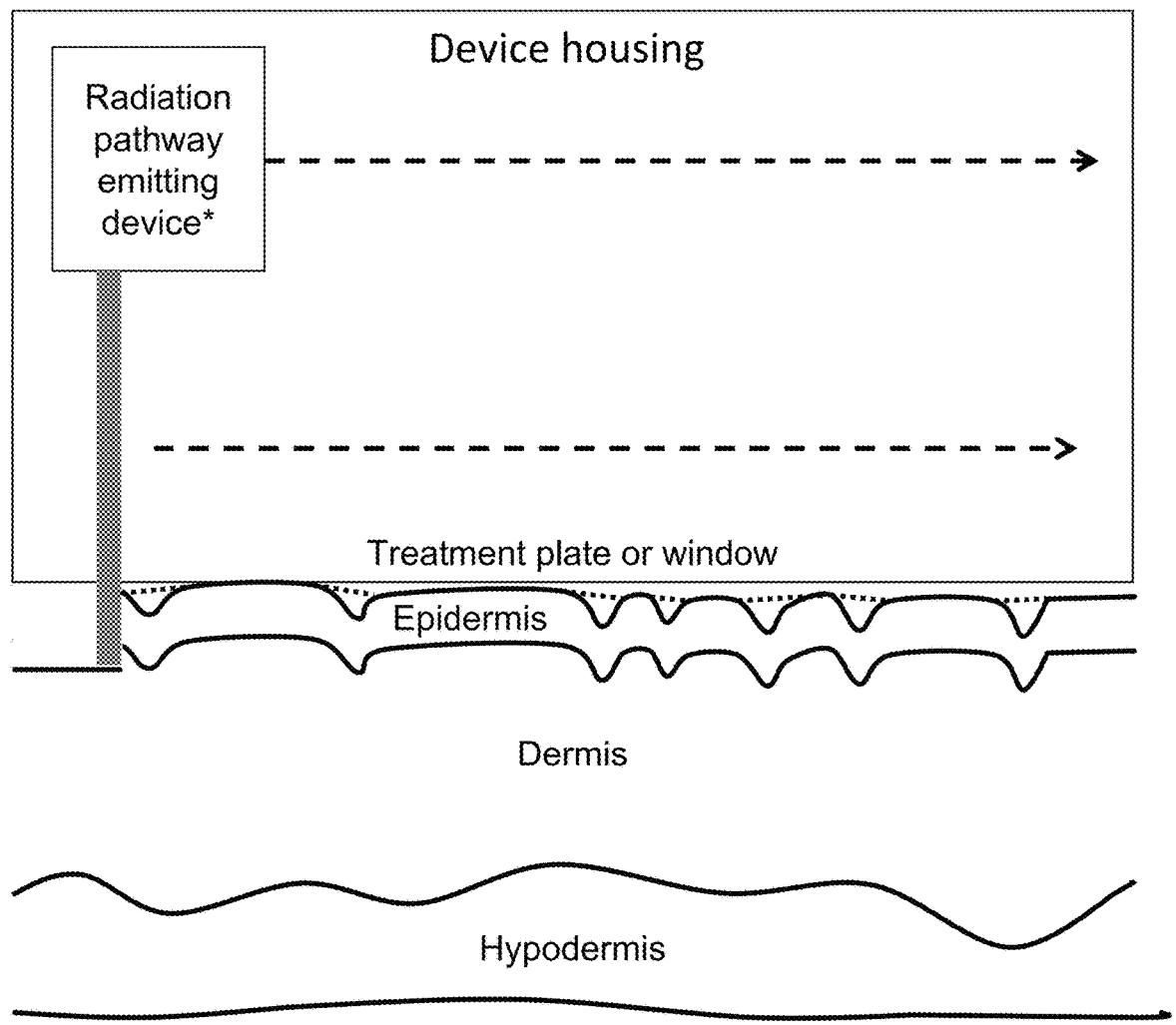
FIG. 7 shows a device housing with a treatment plate or window through which the radiation pathway is delivered to the skin surface.
Figure 15:
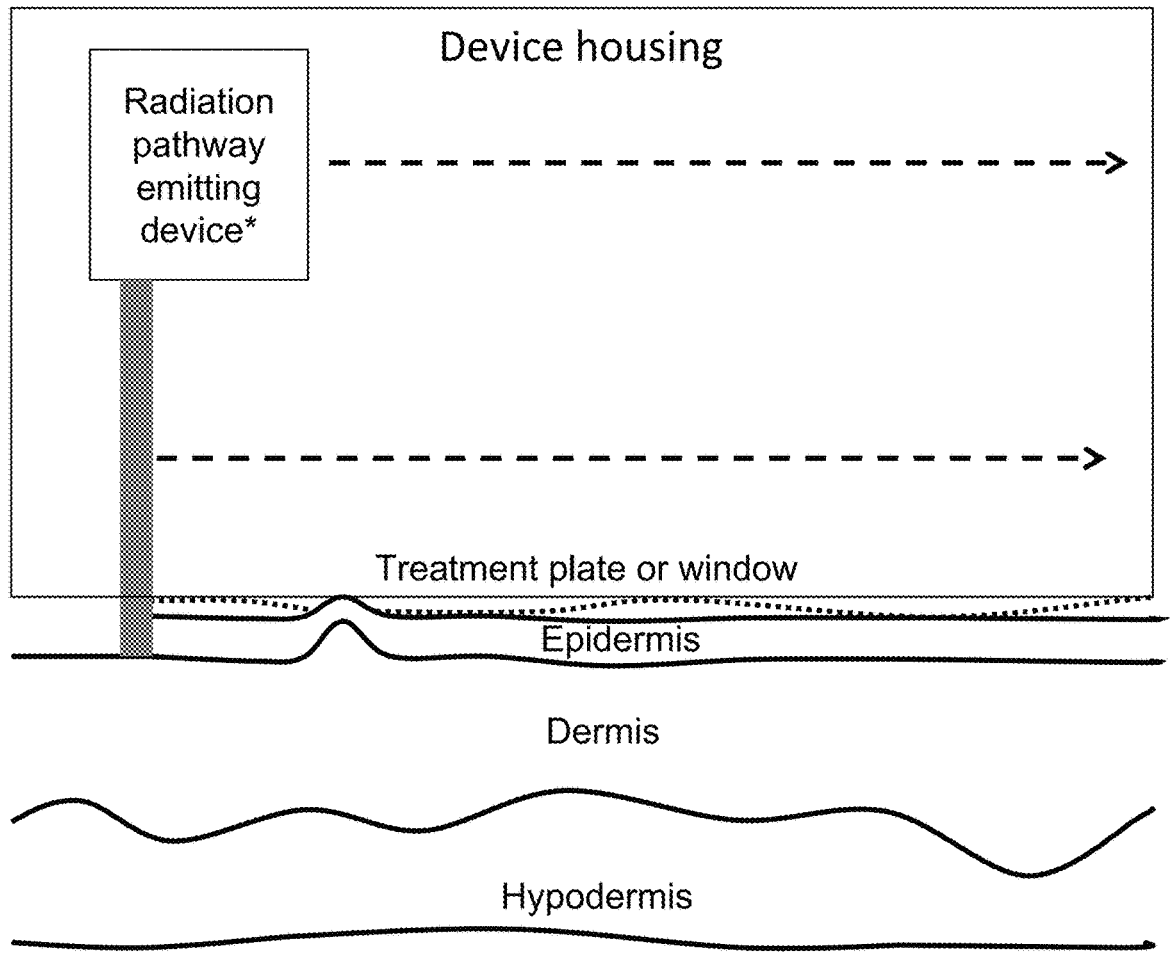
FIG. 15 shows treatment of hypertrophic scarring with a device housing, comprising a radiation pathway emitting device (which may comprise a radiation-emitting device, handset, galvo mirror, or other pathway delivery device), as well as a treatment plate or window.

The device might also include a treatment plate or window to be placed against the skin in order to flatten the skin surface during treatment (see FIGS. 7 and 15). This plate or window may, without limitation, be part of a handset or part of the device itself. The plate or window would be configured to permit the passage of some or all of the radiation to skin surface. Examples of appropriate plate or window materials include calcium fluoride, barium fluoride, lithium fluoride, sapphire, fused silica, quartz, borosilicate crown glass, silicon, germanium, zinc zelenide, and zinc sulfide.

The topical radiation block is a topical material, applied to the surface of the skin prior to treatment of the skin with one or more radiation-emitting devices (see FIGS. 2-6 and 11-14). The block may consist of one or more elements, compounds, mixtures, or other materials capable of blocking some or all of the radiation generated by the applicable radiation-emitting device(s). The block may be in the form of a gas, liquid, powder, soft solid, or hard solid at room temperature immediately prior to its application. Liquid forms of block might include, without limitation, creams, gels, and pastes. Exemplary blocks include, without limitation, tinfoil, aluminum foil, vitamin C (including ascorbic acid and ascorbyl palmitate), vitamin E, beta-carotene, vitamin A, anthocyanins, proanthocyanins, selenium, chelates (such as ortho-phenanthroline, edetic acid [and its salts/derivatives], and dipyridylamine), octyldodecyl neopentanoate, acrylates, octylpropenamide copolymer, aluminum starch octenylsuccinate, aminobenzoic acid, avobenzone, cinoxate, dioxbenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, iron oxide, chromium oxide, talc, mica, polymers, modified chitin, commercial sunscreens and sun blocks, potassium iodine, iophendylate, iohexol, and iopamidol.

The purpose of the topical radiation block is to manage the areas to which the radiation is applied to the skin by allowing the radiation to reach some portions of the skin, while limiting or preventing the radiation from reaching other portions of the skin (see FIGS. 7-9 and 15-17). In the case of atrophic scarring, for example, the block may be deposited selectively into the atrophic indentations, such that the block limits or prevents the radiation from reaching (and thereby ablating) the indentations, but allows the radiation to reach (and thereby ablate) the surrounding skin tissue (see FIGS. 7-9). By ablating only the surrounding tissue, the z of the surrounding tissue is reduced, eventually minimizing or eliminating differences in the skin's topography between the indentations and the surrounding tissue (see FIGS. 7-9).

Depositing the block into atrophic indentations may be achieved by any number of methods. One method would be to apply a thick layer of the block to the entire surface of the treatment area (see FIG. 2) and then remove some or all of the block from the treatment area with a spatula, cloth, sponge, or other device, leaving the highest densities of block only in the indentations (see FIG. 3). Other methods include applying a thin layer of the block to the entire surface of the treatment area with a spatula, cloth, sponge, or other device, leaving the highest densities of block only in the indentations (see FIG. 4) and injecting the block only into the atrophic indentations (see FIG. 5).

In the case of atrophic scarring, the ablation might be gradually reduced at the margins of the treatment area to blend the transition between the ablated region and the non-ablated region outside the treatment area. This might be achieved by gradually reducing the radiation fluence and/or increasing the spot and/or line separation as it approaches the margins.

Figure 16:
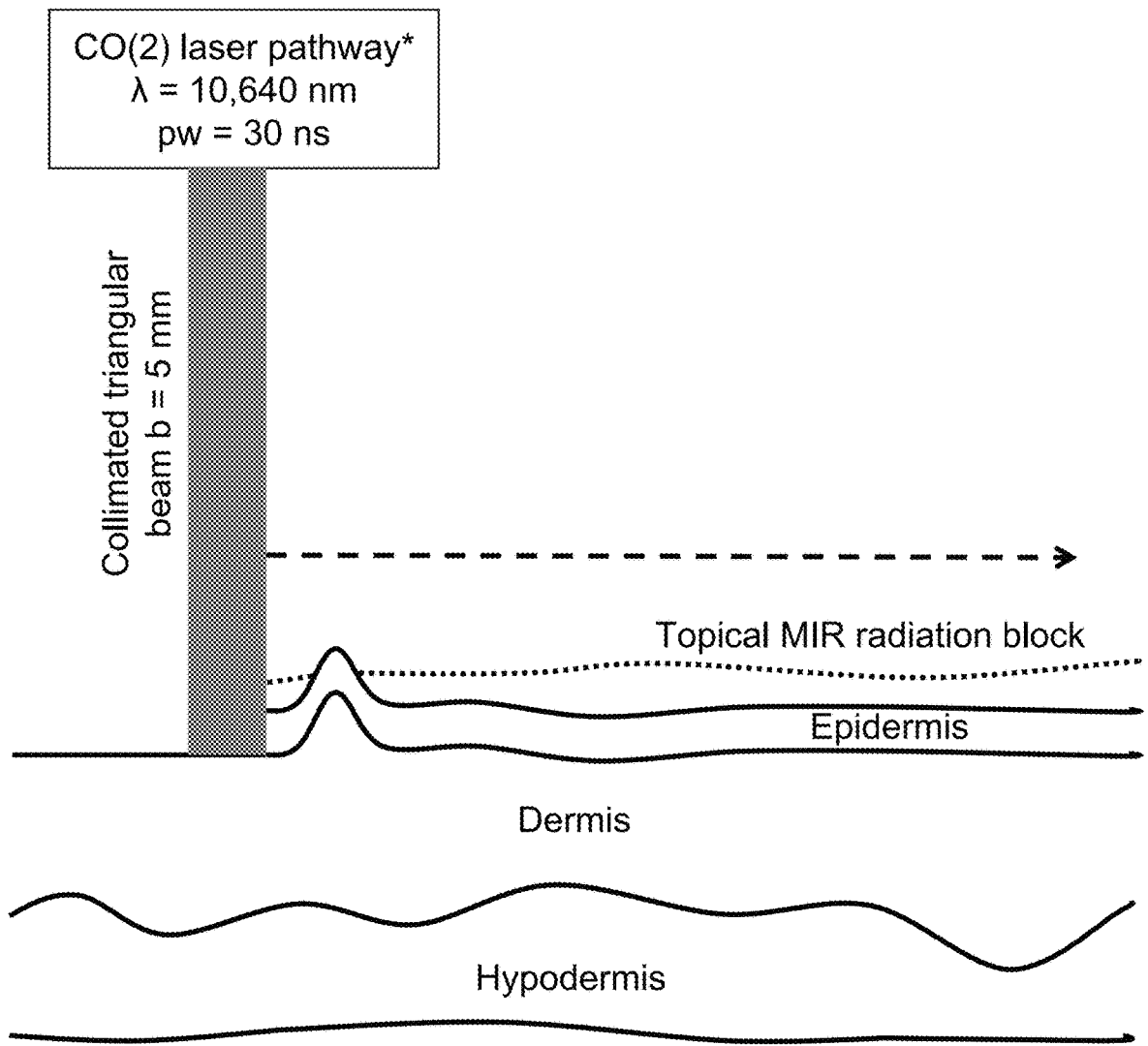
FIG. 16 shows a specific embodiment of the claimed invention, whereby hypertrophic scarring is treated with a CO(2) laser pathway, moved across the skin.
Figure 17:
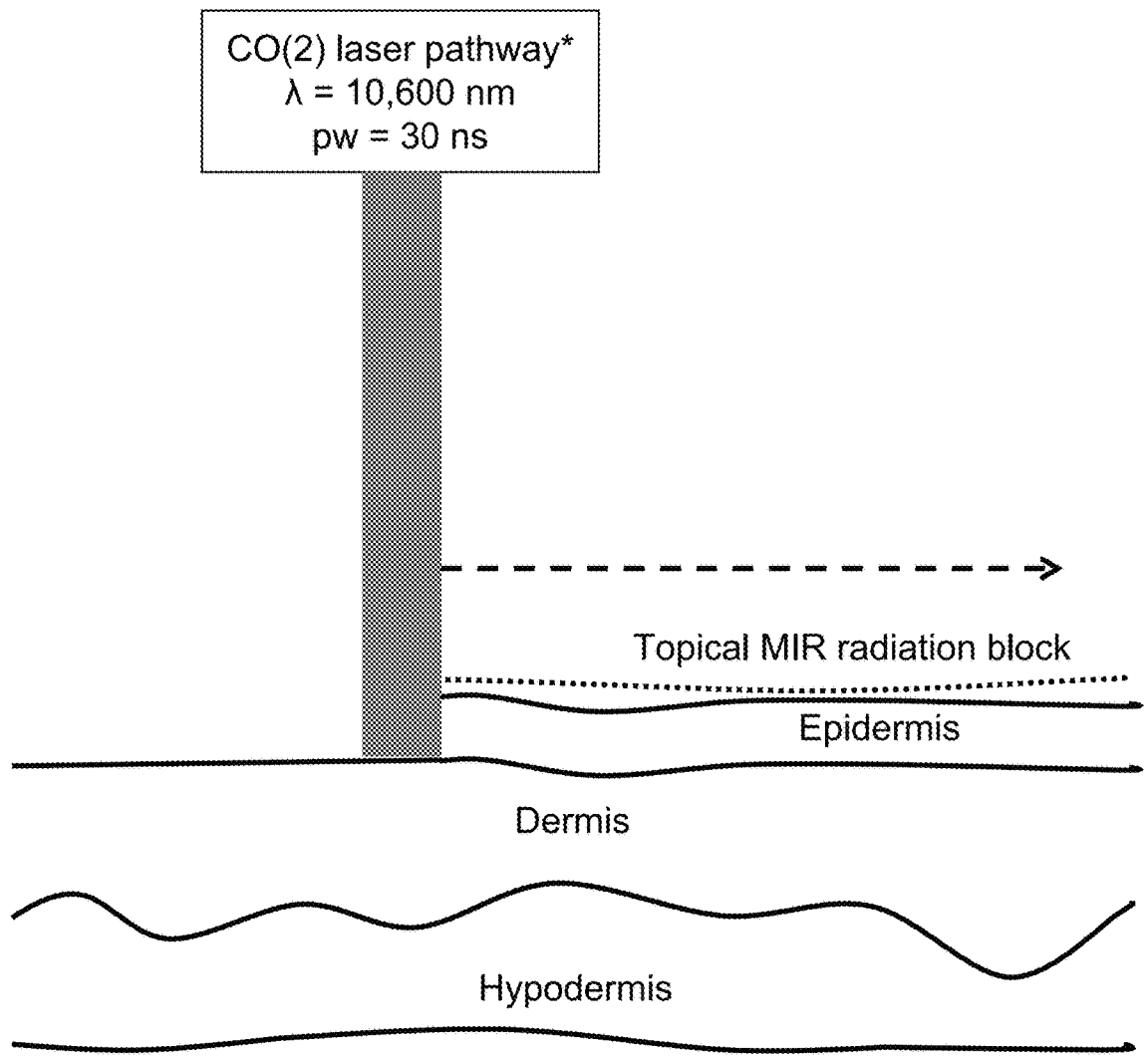
FIG. 17 shows the embodiment of FIG. 16, after partial treatment.

In the case of hypertrophic scarring, the block may be applied selectively to the surrounding tissue, such that the block limits or prevents the radiation from reaching (and thereby ablating) the scars, but allows the radiation to reach (and thereby ablate) the scars (see FIGS. 15-17). By ablating only the scars, the z of the scars is reduced, eventually minimizing or eliminating differences in the skin's topography between the scars and the surrounding tissue (see FIGS. 16-17).

Applying the block to skin with hypertrophic scarring may also be achieved by any number of methods. One method would be to apply the block thickly to the entire affected area and then apply the treatment plate or window to the treatment area in order to squeeze the block from the raised scar surfaces, but not form the unscarred skin surfaces (see FIG. 15). Alternatively, the block might be applied thickly to the entire affected area (see FIG. 11) and then removed from the raised scars with a spatula, cloth, sponge, or other device, leaving the highest densities of block only on the unscarred skin surface (see FIG. 12). Another method would be to apply the block thinly with a spatula, cloth, sponge, or other device such that a layer remains on the unscarred skin surface, but not on the surface of the raised scars (see FIG. 13).

The present invention may be performed on any area of the body covered by skin, including, without limitation, the face, neck, chest, back, shoulders, buttocks, arms, legs, feet, hands, and scalp.

In one embodiment of the invention, a patient presents with atrophic acne scars. The patient lies down on a treatment table. A lidocaine and/or prilocaine eutectic mixture might be applied to the treatment area in the form of a cream (e.g., EMLA Cream, AstraZeneca Global, London, England) or a cellulose disk (e.g., EMLA Dermal Patch, AstraZeneca Global, London, England) to reduce pain during treatment. A sedative might be administered as well, depending upon the patient's pain tolerance.

Figure 2:
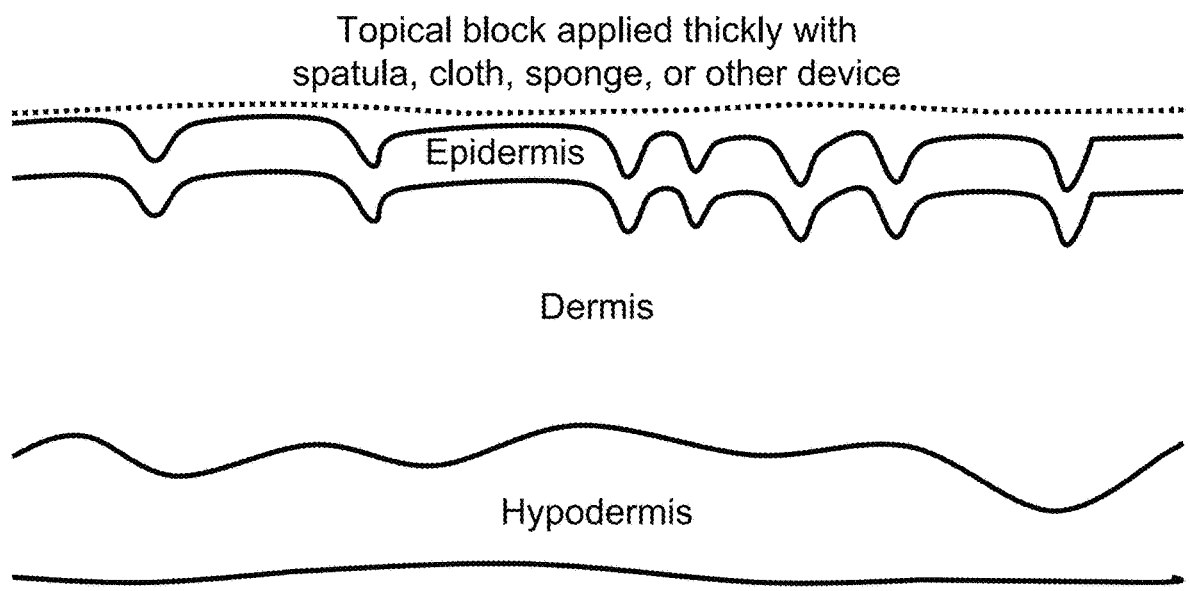
FIG. 2 shows a topical radiation block applied thickly to an atrophic scar treatment area with a spatula, cloth, sponge, or other device.
Figure 3:
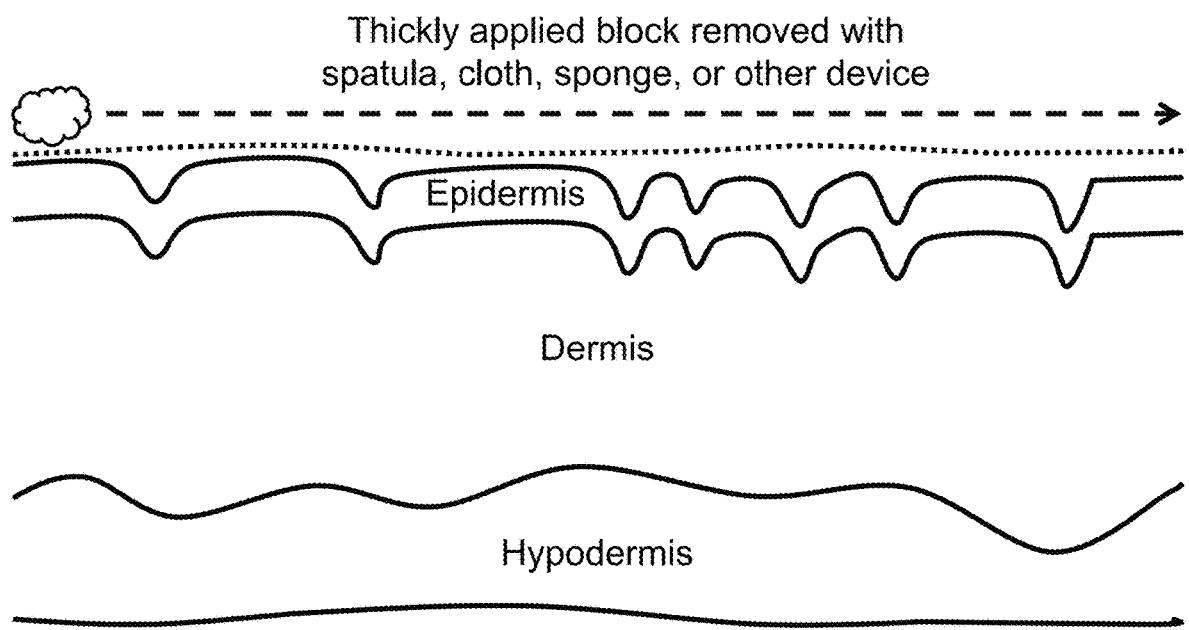
FIG. 3 shows a thickly applied topical radiation block removed from an atrophic scar treatment area with a spatula, cloth, sponge, or other device moved across the skin.
Figure 4:
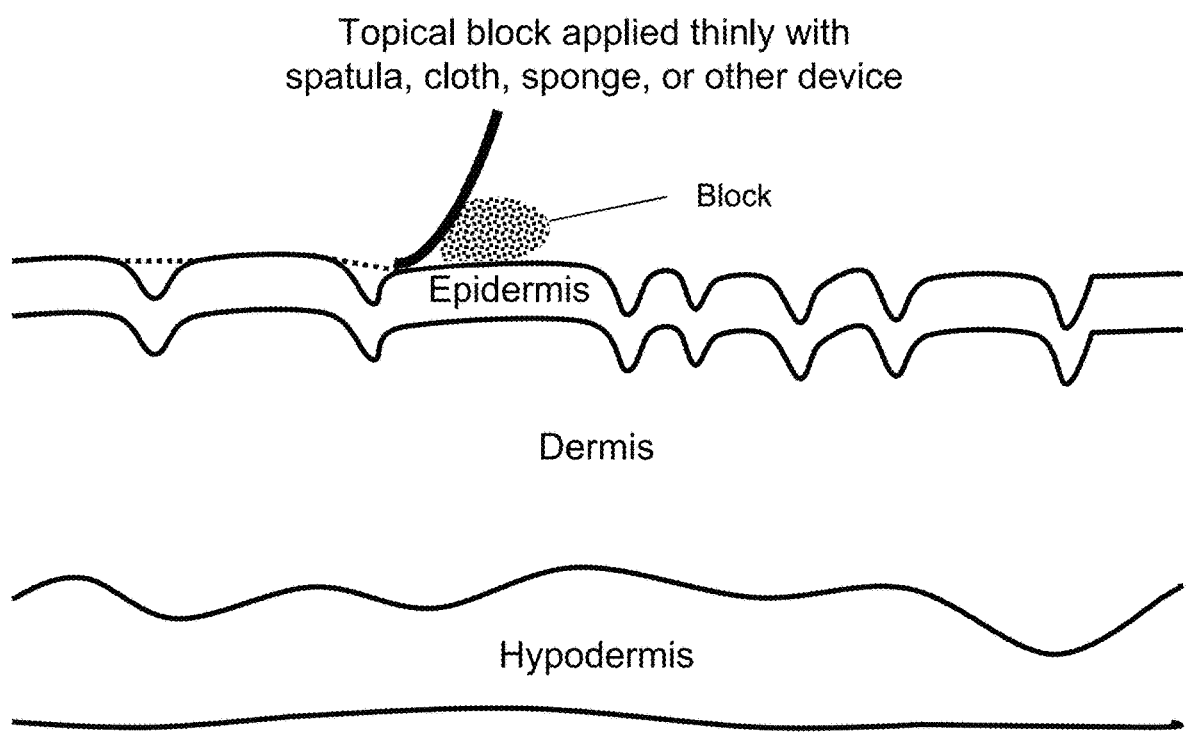
FIG. 4 shows a topical radiation block applied thinly to an atrophic scar treatment area with a spatula, cloth, sponge, or other device moved across the skin.
Figure 5:
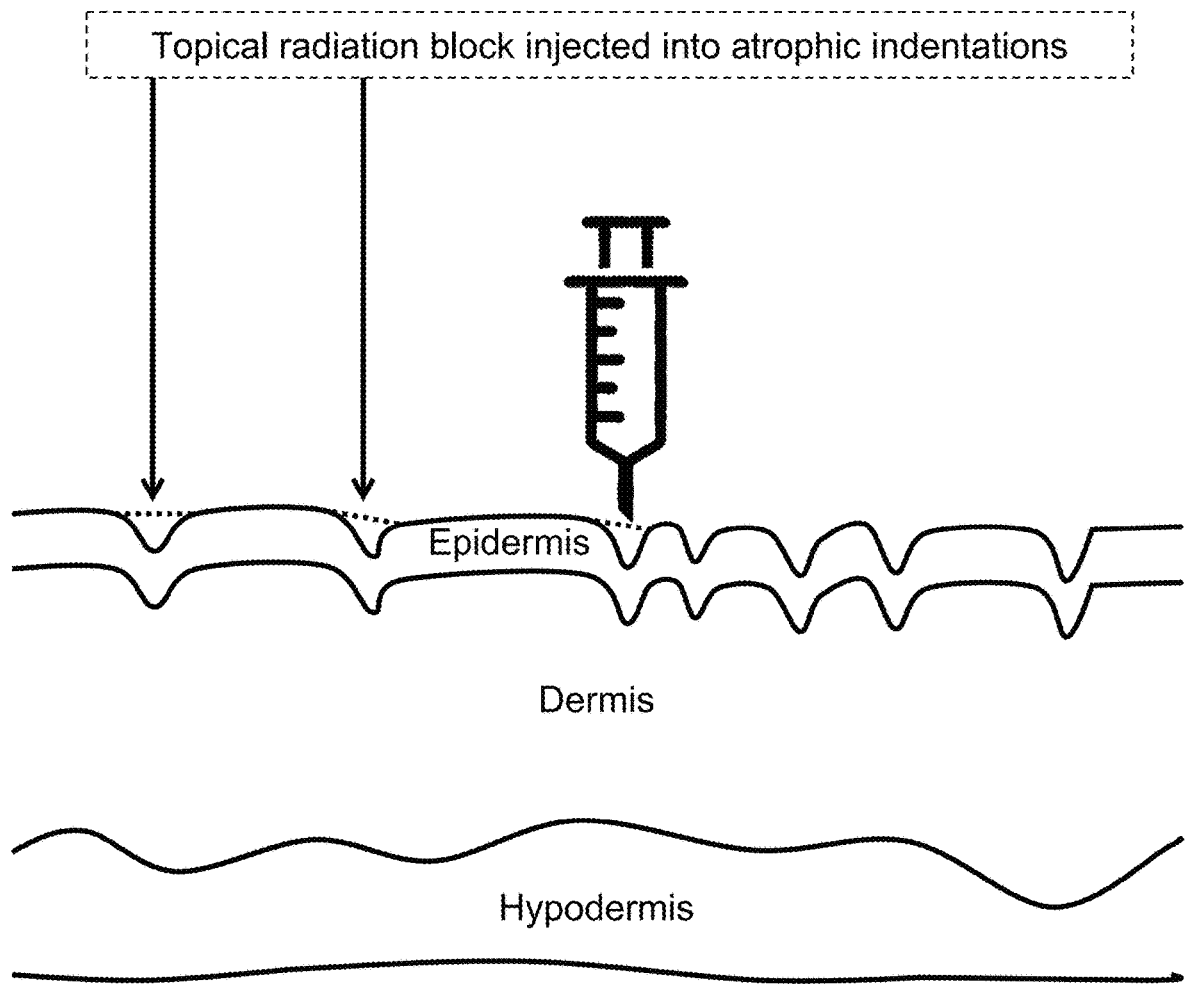
FIG. 5 shows a topical radiation block injected into atrophic indentations.
Figure 6:
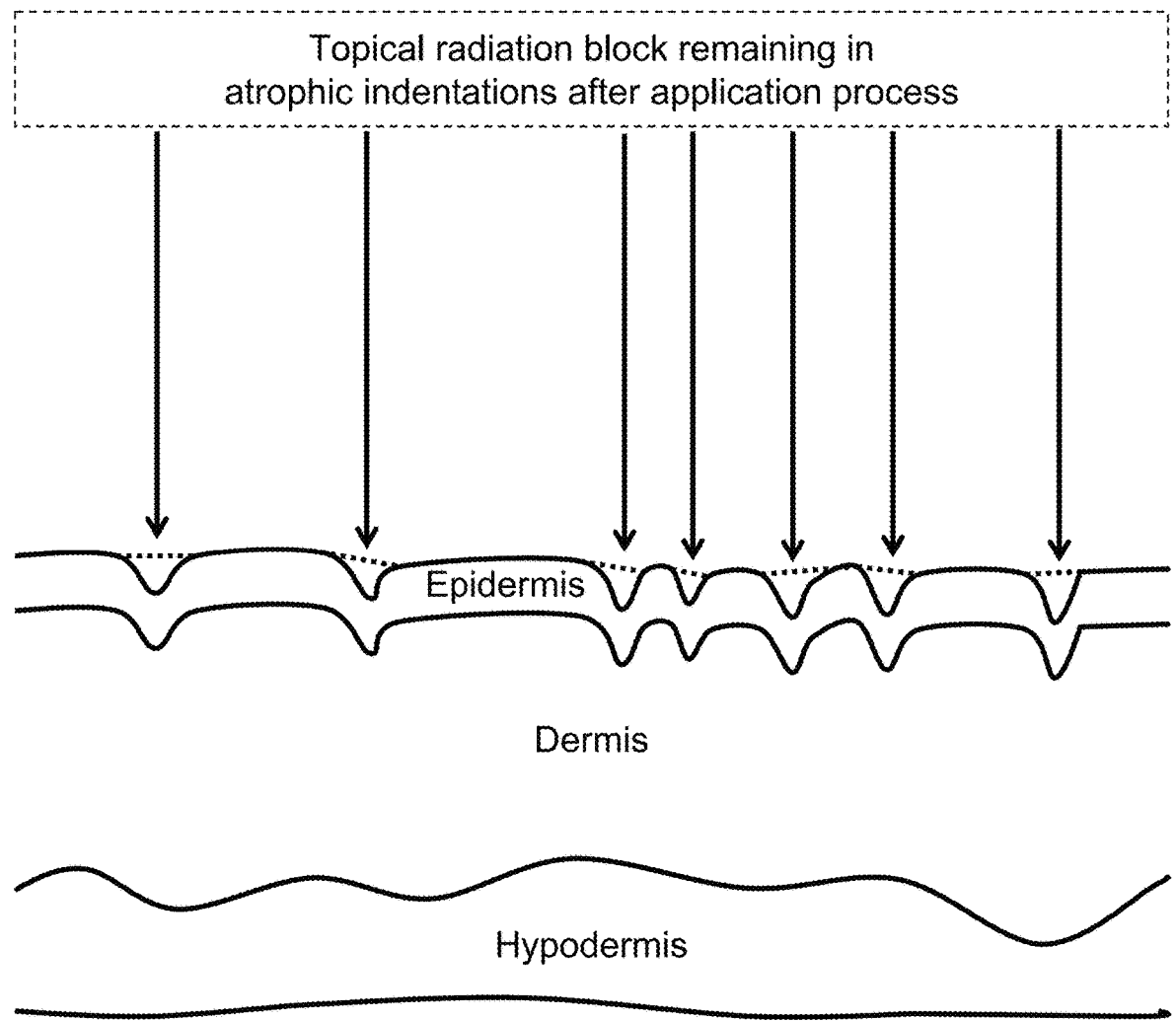
FIG. 6 shows a topical radiation block remaining in atrophic indentations after the application process.

Once the treatment area is numb and/or the sedative has taken effect, the topical radiation block is applied to the treatment area (see FIG. 2). A block that reflects or absorbs wavelengths in the UVC (100-290 nm) range is used (see laser specifications below). The treatment area is a contiguous area of the skin that includes both atrophic scars and surrounding skin (see FIG. 2). If large areas of skin are to be treated, the technician may choose to treat only one smaller area or multiple smaller non-contiguous areas over multiple treatment sessions to improve healing time, reduce pain, and mitigate the risk of infection and systemic side effects. The block is applied evenly to the treatment area (see FIG. 2). Depending upon the material used, the technician might allow some time to pass for the block to bond to the skin surface, harden, desiccate, or otherwise change. A spatula, cloth, sponge, or other device is then drawn across the treatment area to remove some or all of the block from the non-scarred skin surface, leaving block in the atrophic indentations (see FIG. 3).

One or more additional topical compounds may be applied to some or all of the treatment area before or after some or all of the block is removed from the non-scarred skin surface. By way of example, a compound for insulating or cooling the skin surface, for regulating the heat at the skin surface, for improving radiation absorption might be applied to the treatment area, and/or for managing pain. An example of a cooling compound commonly used with radiation skin treatments is the SkinCool Cryogen canister (Skin Cool Center, Chantilly, Va.).

Figure 8:
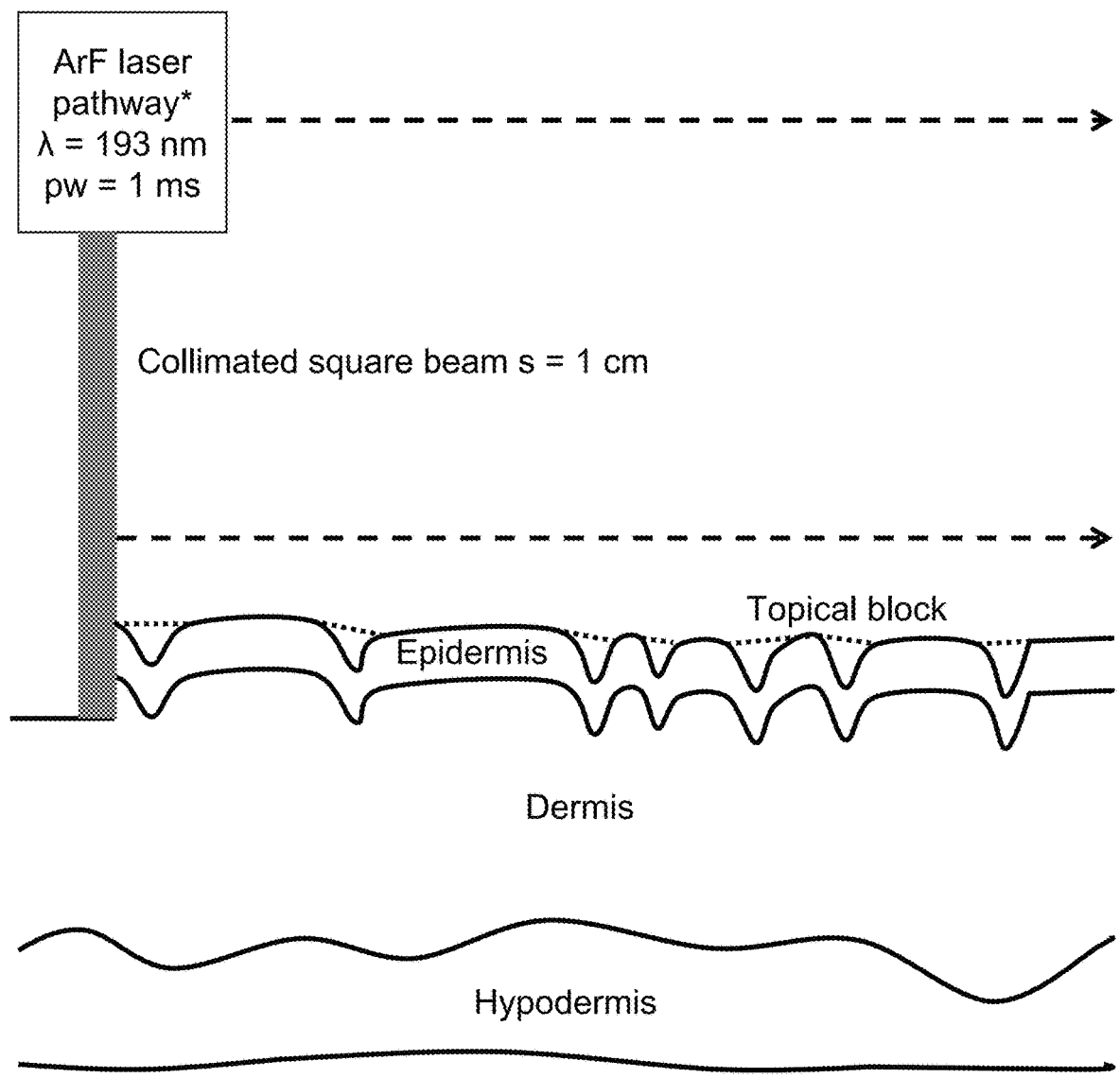
FIG. 8 shows a specific embodiment of the claimed invention, whereby atrophic scarring is treated with an ARF laser pathway, moved by hand across the skin.
Figure 9:
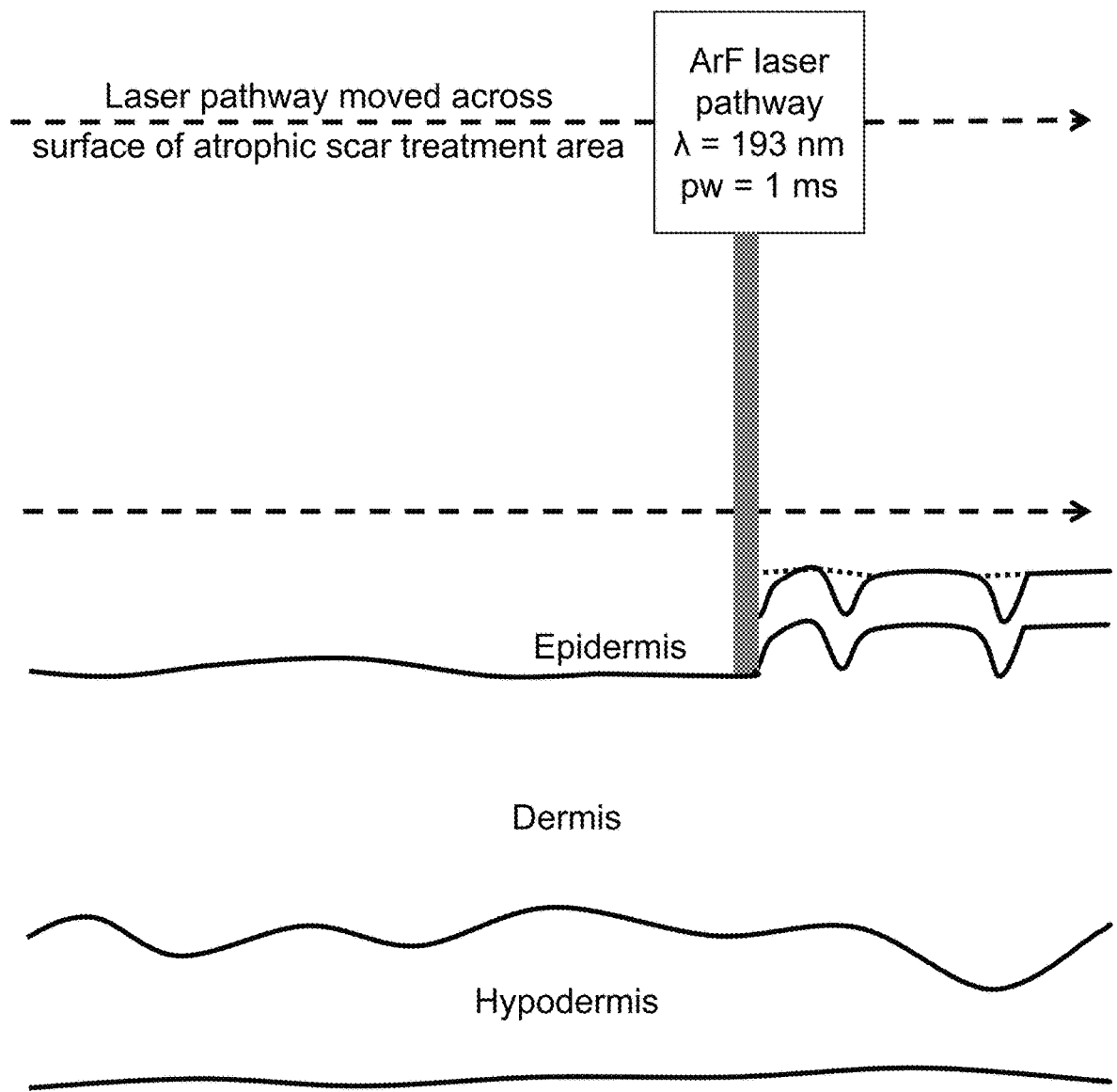
FIG. 9 shows the embodiment of FIG. 8, after partial treatment of the treatment area.

The radiation-emitting device is then applied to the treatment area (see FIG. 8). A pulsed excimer ArF laser generating a 193 nm wavelength is used. The pulse width is 1 ms. The radiation pathway is collimated, and the spot is square in shape with a side of 1 cm. The spots are applied by hand, with each line and spot immediately adjacent and tangent to the preceding line or spot. The laser energy ablates more of the skin tissue from which the topical material was removed and less of the skin tissue where the topical material remains (see FIG. 9). Both the epidermis and a portion of the dermis are ablated. This procedure may be repeated as necessary at whatever time intervals the technician deems appropriate, i.e., anywhere from seconds to days, weeks, or months apart.

Figure 10:
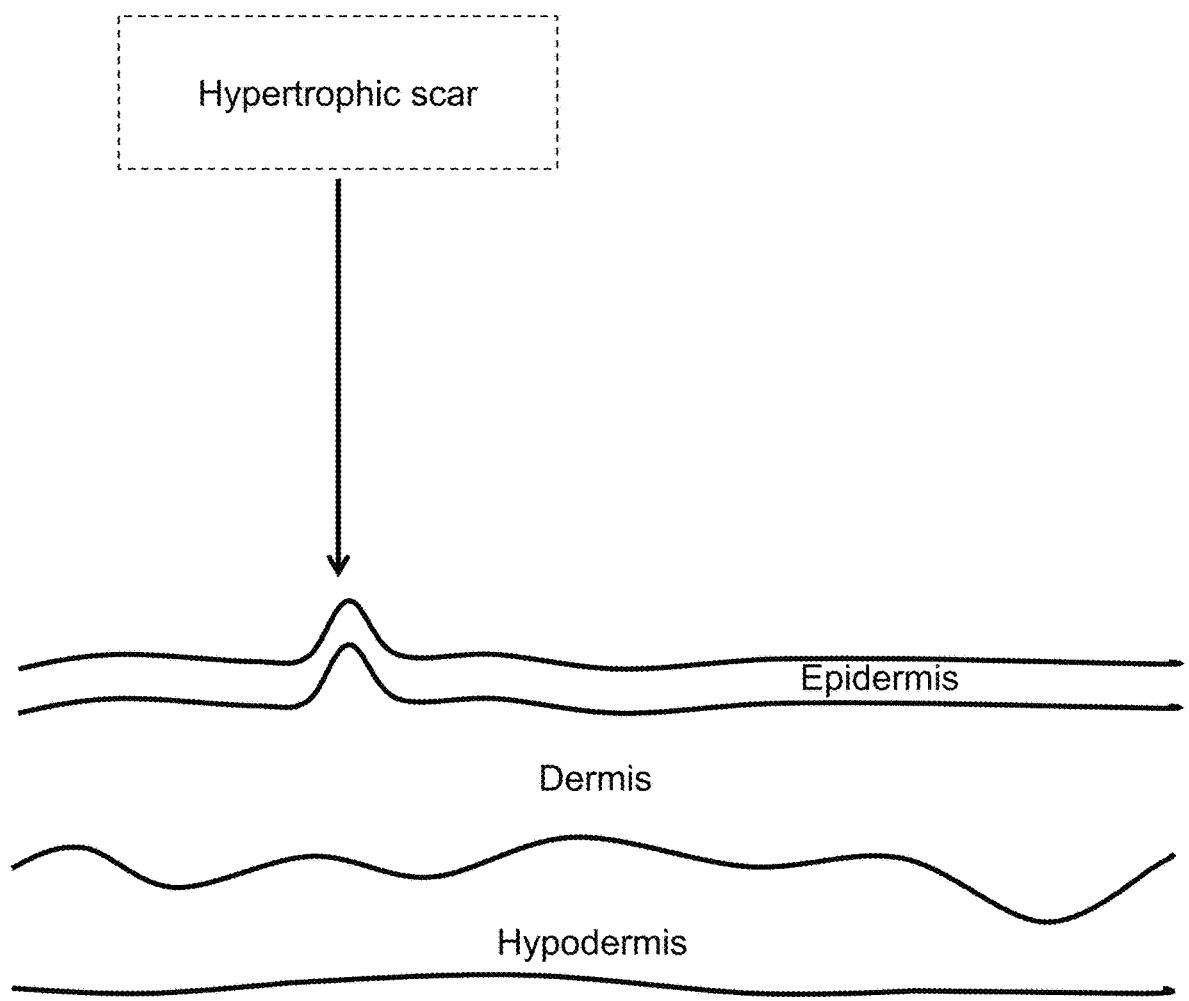
FIG. 10 shows a hypertrophic scar.
Figure 11:
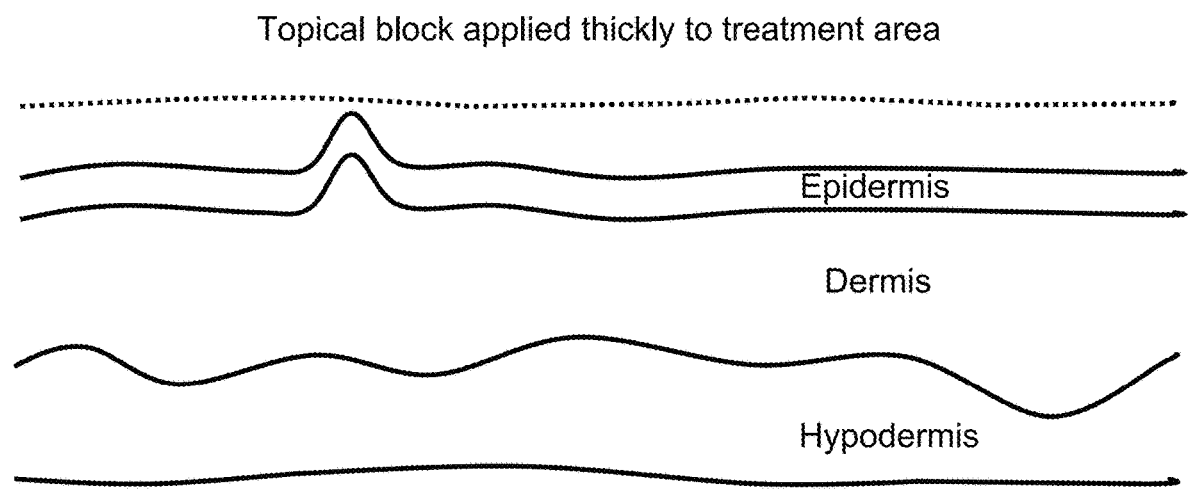
FIG. 11 shows a topical radiation block applied thickly to a hypertrophic scar treatment area with a spatula, cloth, sponge, or other device.
Figure 12:
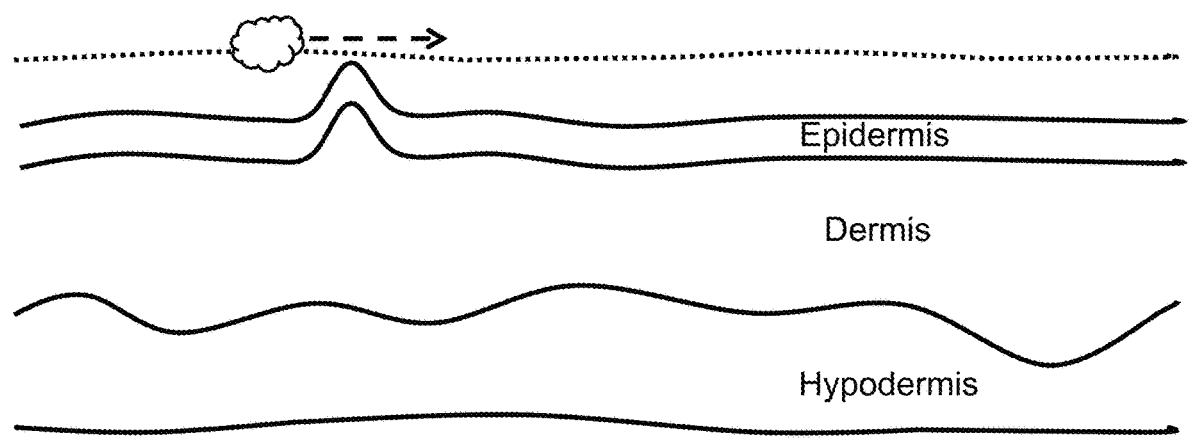
FIG. 12 shows a thickly applied topical radiation block removed from a hypertrophic scar treatment area with a spatula, cloth, sponge, or other device moved across the skin.
Figure 13:
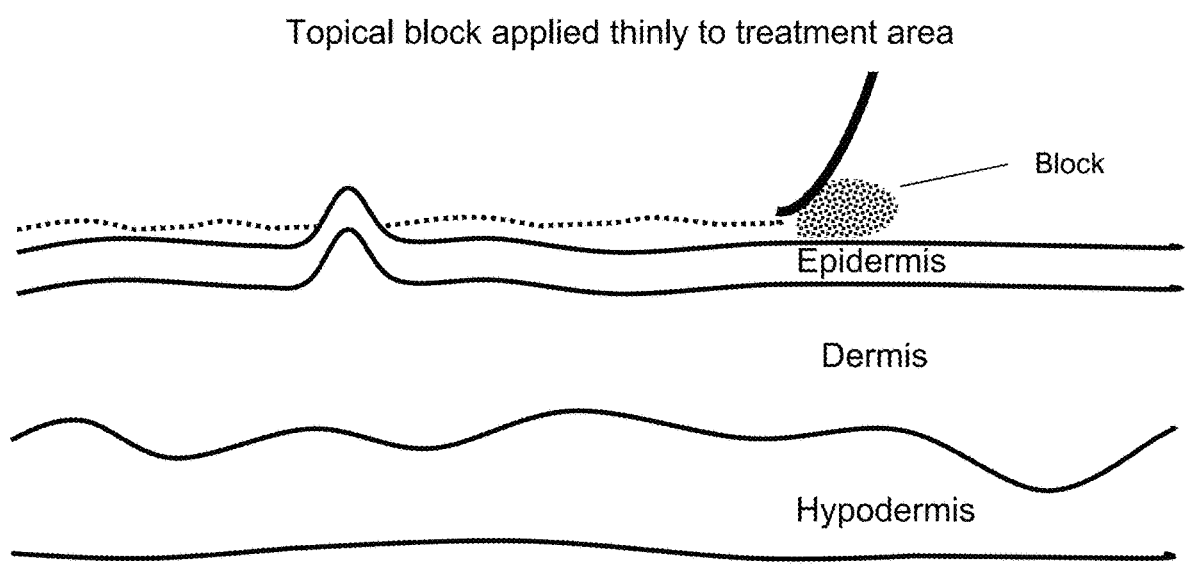
FIG. 13 shows a topical radiation block applied thinly to a hypertrophic scar treatment area with a spatula, cloth, sponge, or other device moved across the skin.
Figure 14:
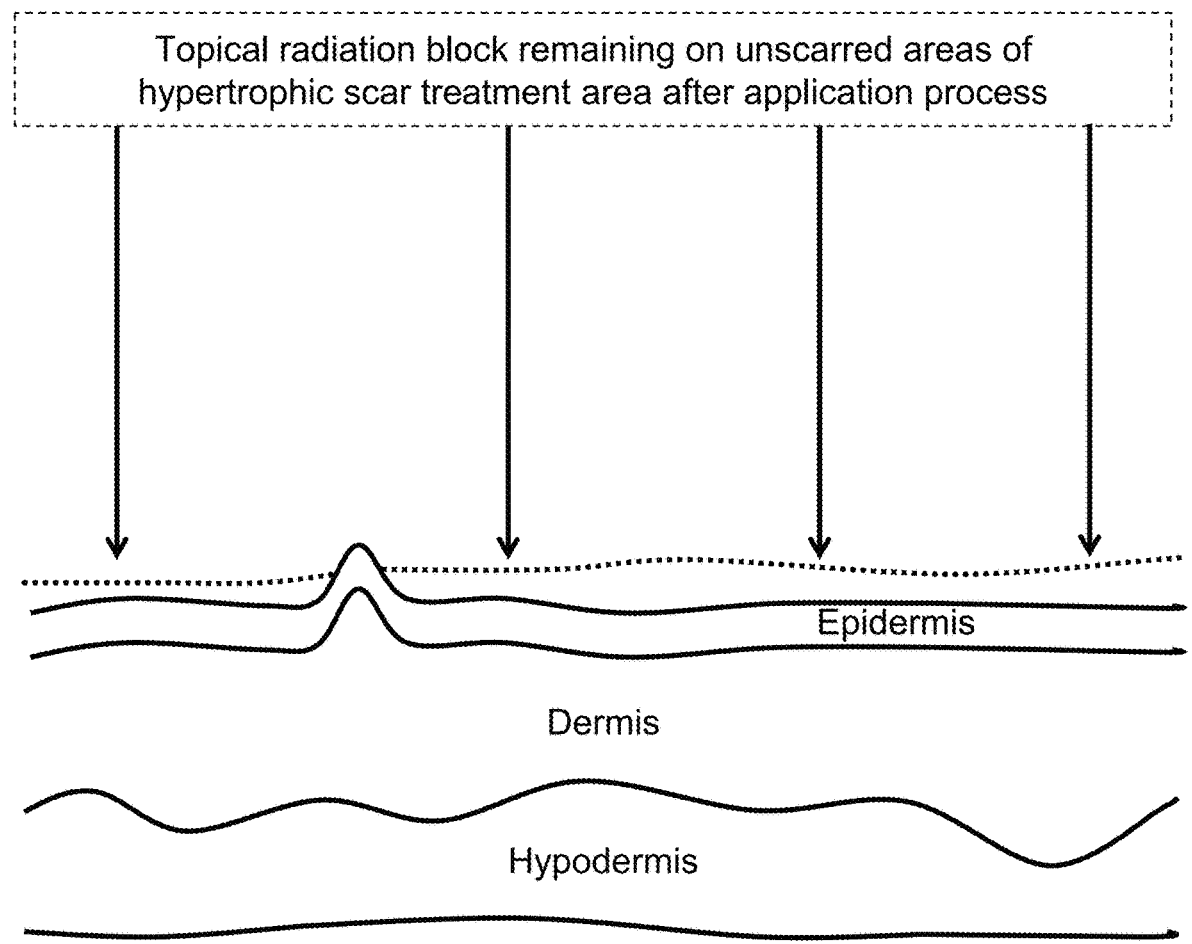
FIG. 14 shows a topical radiation block remaining on the unscarred areas of the hypertrophic scar treatment area after the application process.
Figure 18:
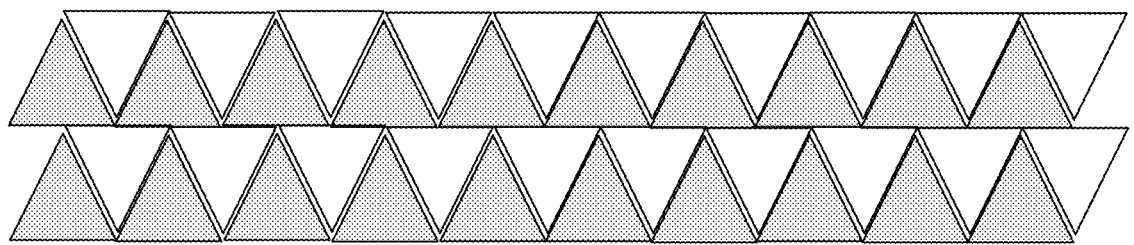
FIG. 18 shows an exemplary treatment pattern for the embodiment of FIG. 16.

In another embodiment of the invention, a patient presents with a hypertrophic scar from an injury (see FIG. 10). The topical material is a liquid that is applied thickly to the skin (see FIG. 11) and then wiped, rubbed, or scraped off or otherwise removed such that a thicker layer of the material remains in the areas adjacent to the scar than on the scar itself (see FIGS. 12-14). The radiation-emitting device is a pulsed CO(2) laser generating a 10,640 nm wavelength (see FIG. 16). The pulse width is 30 ns. The radiation pathway is collimated, and the spot size is triangular in shape with a base of 5 mm. Because the laser wavelength falls within the mid-infrared portion of the radiation spectrum, a mid-infrared blocking agent is used as the topical material. The radiation pathway is guided by computer-driven galvos mirrors (see FIG. 16). The spots are applied with the bases immediately adjacent the preceding spot, and each line is then repeated with the triangle inverted and inserted into the untreated line space. Each line is treated in the same manner, immediately adjacent the preceding line (see FIG. 18). The laser energy ablates more of the hypertrophic scar tissue from which the topical material was removed and less of the adjacent tissue where the topical material remains (see FIG. 17). Both epidermis and dermis are ablated.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method for improving the appearance of scars within a predetermined treatment area of skin, comprising:
providing a laser radiation-emitting device, wherein the device is configured to deliver laser radiation along a laser radiation pathway to the treatment area, and the radiation is configured to ablate the skin; and
prior to delivery of the radiation pathway to the treatment area, applying at least one layer of a topical laser radiation block to the treatment area, such that at least one of:
in the case of atrophic scar tissue, (a) the layer is thicker within the scar tissue, thereby limiting or preventing the radiation from reaching and ablating the scar tissue, and (b) at least one of thinner at or absent from unscarred tissue within the treatment area, thereby allowing the radiation to reach and ablate the unscarred tissue, or
in the case of hypertrophic scar tissue, (a) the layer is at least one of thinner at or absent from the scar tissue, thereby allowing the radiation to reach and ablate the scar tissue, and (b) thicker at unscarred tissue within the treatment area, thereby limiting or preventing the radiation from reaching and ablating the unscarred tissue.

2. The method of claim 1, wherein the manner by which the block is applied to the treatment area comprises at least one of: applying the block to the entire treatment area and removing none of the block prior to delivery of the radiation pathway; applying the block to the entire treatment area and then removing a portion of the block prior to delivery of the radiation pathway; or applying the block to only a portion of the treatment area prior to delivery of the radiation pathway.

3. The method of claim 1, wherein the radiation-emitting device is a laser, the laser comprises a gain medium, and the gain medium comprises at least one of excimer or $CO(2)$.

4. The system of claim 1, wherein the plate or window is placed against the skin comprising the treatment area, and while the plate or window remains stationary against the skin, the radiation pathway passes through the plate or window and is guided about the treatment area by at least one of a computer-driven fiber-optic cable or a computer-driven mirrors.

5. The method of claim 1, wherein the radiation-emitting device comprises a treatment plate or window.

* * * * *